United States Patent [19]

Ryczek et al.

[11] Patent Number: 5,150,174
[45] Date of Patent: Sep. 22, 1992

[54] PHOTOELECTRIC COLOR SENSOR

[75] Inventors: Lawrence J. Ryczek, Oconomowoc; Michael G. Taranowski, Milwaukee; Eugene F. Duncan, Wauwatosa, all of Wis.

[73] Assignee: Eaton Corporation, Cleveland, Ohio

[21] Appl. No.: 674,247

[22] Filed: Mar. 25, 1991

[51] Int. Cl.$^5$ .................................. G01J 3/50
[52] U.S. Cl. .................................. 356/402; 250/226; 356/406; 356/425; 356/446
[58] Field of Search ............... 356/402, 406, 407, 408, 356/420, 425, 430, 431, 445–448; 250/226

[56] References Cited

U.S. PATENT DOCUMENTS

| | | | |
|---|---|---|---|
| 4,568,191 | 2/1986 | Barry | 356/446 |
| 4,755,058 | 7/1988 | Shaffer | 356/408 |
| 4,823,169 | 4/1989 | Ogura | 356/446 |
| 4,917,500 | 4/1990 | Lugos | 356/425 |
| 4,986,665 | 1/1991 | Yamanishi et al. | 356/425 |

Primary Examiner—F. L. Evans
Attorney, Agent, or Firm—R. A. Johnston

[57] ABSTRACT

At least one pair of light emitting diodes (LEDs) is disposed to direct a beam of common discrete chromaticity each to a separate target area located at different distances from a centrally disposed photodetector. Upon pulsing of the diodes at a common time, the photodetector receives the sum of the diffused light reflected from a target disposed at a location between the separate target areas to substantially reduce the affects of variation in distance of a target from the photodetector. The photodetector output is corrected for the effects on the LEDs of variations in ambient temperature.

7 Claims, 6 Drawing Sheets

PHOTOELECTRIC COLOR SENSOR

BACKGROUND OF THE INVENTION

The present invention relates to devices employed for monitoring variations in color of objects such as articles of manufacture for which it is desired to maintain consistency of color or, stated in other words, detect excessive variation in the color of the articles.

Color detectors of this sort can be employed on assembly lines to monitor the variation of color of articles of manufacture during the final stage of quality inspection as, for example, monitoring the variation in color of pharmaceutical capsules to prevent inclusion of capsules of the wrong color in a package containing capsules color-coded for a specific pharmaceutical content. In such an application, it is commonplace to have the color detector disposed at a stationary position along a moving conveyor for inspecting articles as they pass the stationary detector. Such an arrangement often results in a variation in the distance of the surface of the targeted article from the detector, which affects the intensity of the diffused reflected light from the targeted article; and, thus affects the level of reflected light detected by the sensor and usually results in an erroneous signal from the detector.

Thus, it has been desired to find a way or means of accommodating variations in the distance of an article to be monitored for color variation from the color sensor or detector in a manner which is simple and inexpensive, and may be employed on a continuous basis for sensing variations in color in articles in a mass-production application. It has further been desired to provide such accommodation for variations in distance for sensing color of a target article without the need for plural detectors each calibrated to sense the color of an object at a different distance.

SUMMARY OF THE INVENTION

The present invention provides a single color sensor employing a photo detector which may be positioned to sense variations in color of articles passing by the detector within a predetermined range of distances from the detector. The sensor of the present invention utilizes a pair of light-emitting diodes (LEDs) disposed on opposite sides of a photo detector and angled to direct a beam of light of common discrete chromaticity onto the target. Each beam of the LED is directed to a target area in line with the photo detector, but located at differing predetermined distances from the photo detector. A target object passing the photo detector in the zone or region intermediate the two target areas causes the photo detector to receive the optical sum of the diffused reflected light from the target of both of the LEDs of the pair. Thus, as the distance of the target from the detector varies within the zone between the target areas of each LED, the intensity of the sum of the reflected light remains relatively constant. The detector thus primarily detects only variations due to changes in color of the target; and, thus, a single detector may be employed which can accommodate variations in the distance of the target from the detector.

Preferably, a plurality of pairs of LEDs are provided around the detector with each pair emitting beams of common chromaticity which is different from any other pair. The output of the photo detector may be averaged for the reflected light of each pair of beams to detect any variation in the color of the reflected light within the frequency band of the discreet chromaticity of each pair. Where pairs of diodes emitting red, green, and blue beams are employed, this arrangement provides greater sensitivity of color variations in the visible spectrum, thereby emulating the color detection characteristics of the human eye.

The circuitry of the present invention for detecting and amplifying the signal from a photo detector includes circuitry which can correct for change in the intensity of the beams emitted by the LEDs due to variations in ambient temperature.

The present invention thus provides a unique and novel color sensor employing a photo detector which responds to the sum of diffused reflected light from a pair of LEDs emitting beams of common chromaticity to target regions of differing distances from the detector, thereby providing a generally constant intensity to light reflected from a target passing the detector in a zone intermediate the predetermined target distances. The sensor of the present invention thus accommodates variations in distance of a target object as it passes the photo detector.

DETAILED DESCRIPTION

Figure 1:
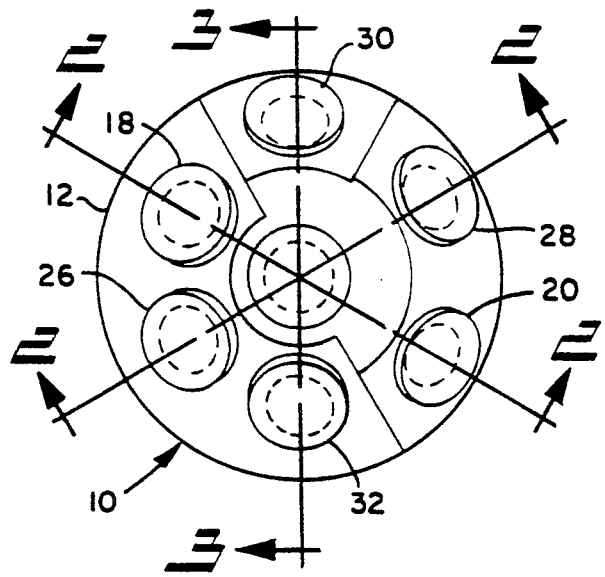
FIG. 1 is a plan view of the photo detector of the present invention.

Referring to FIG. 1, the sensor assembly of the present invention is indicated generally at 10, and has a mounting block or base 12 with a generally circular configuration which may be mounted in any suitable holder (not shown) for positioning the device at a location for sensing the color of a number of articles passing the detector.

Figure 2:
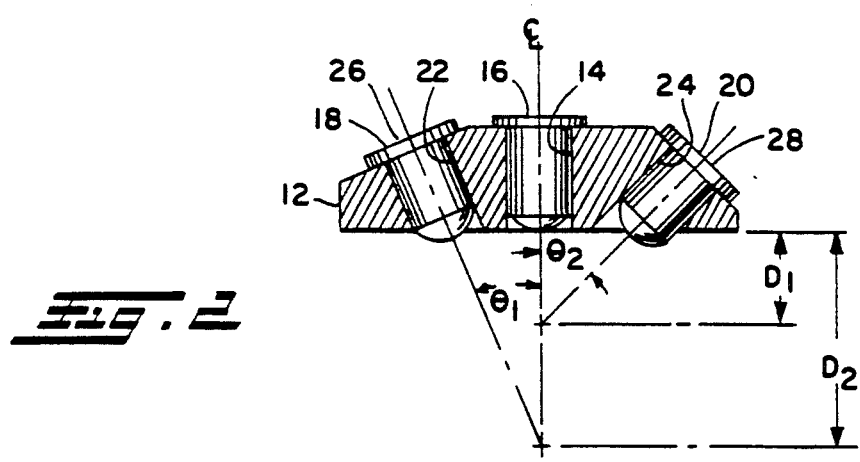
FIG. 2 is a cross-section taken along section indicating lines 2—2.
Figure 3:
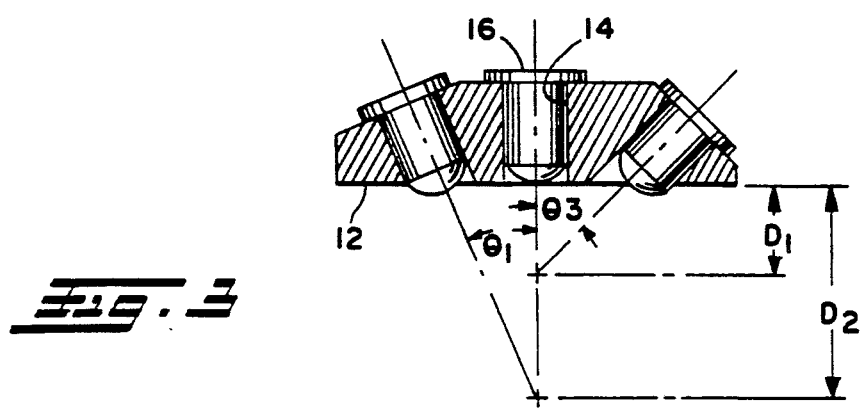
FIG. 3 is a view similar to FIG. 2, taken along section indicating lines 3—3 of FIG. 1.
Figure 5:
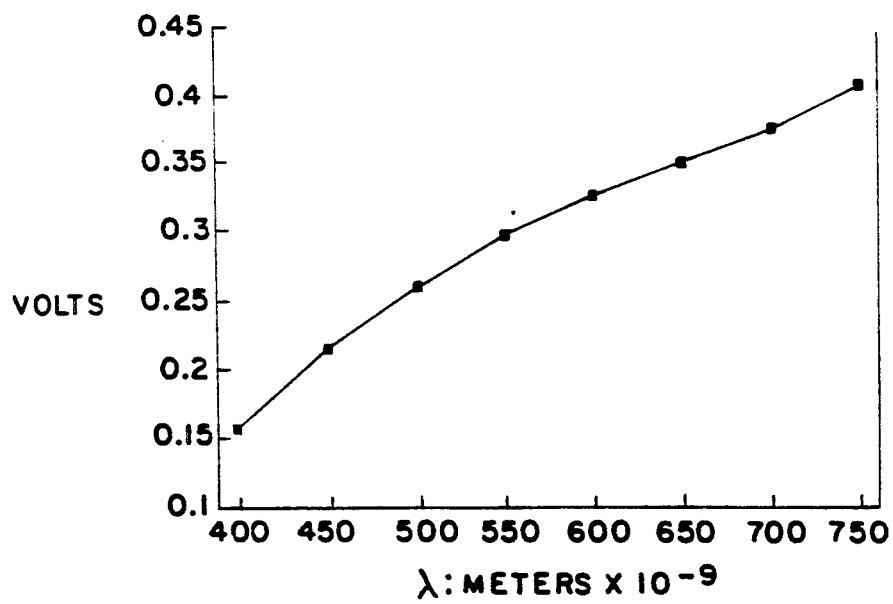
FIG. 5 is a plot of the signal output of the photo detector of the present invention, plotted as a function of wavelength of detected light.

Referring to FIGS. 1 through 3, body 12 has a mounting aperture 14 provided centrally therethrough which has received therein a photo detector device 16 which is arranged to have light directed upwardly as against the underside of body 12 impinge on the detector 16. In the presently preferred practice, detector 16 comprises any commercially available photo detector; however, an OP-805 solid state type device has been found to be particularly satisfactory. The signal output characteristics of the detector 16 are shown in FIG. 5 with the signal strength in volts plotted as the ordinate, and the wavelength in nanometers of the light in the detected region plotted as the abscissa.

A pair of angularly disposed LEDs 18, 20 are disposed diametrically opposed on opposite sides of the detector 16 with the diode 18 inclined at an angle $\theta_1$ to the center line of the aperture 14. LED 20 is inclined at an angle $\theta_2$ to the center line of aperture 14.

The light beam emitted from LED 18 intersects the centerline at a distance $D_2$ from the undersurface of the base 12; and, the light beam emitted from LED 20 intersects the center line at the distance $D_1$ from the undersurface of the base 12.

Figure 6:
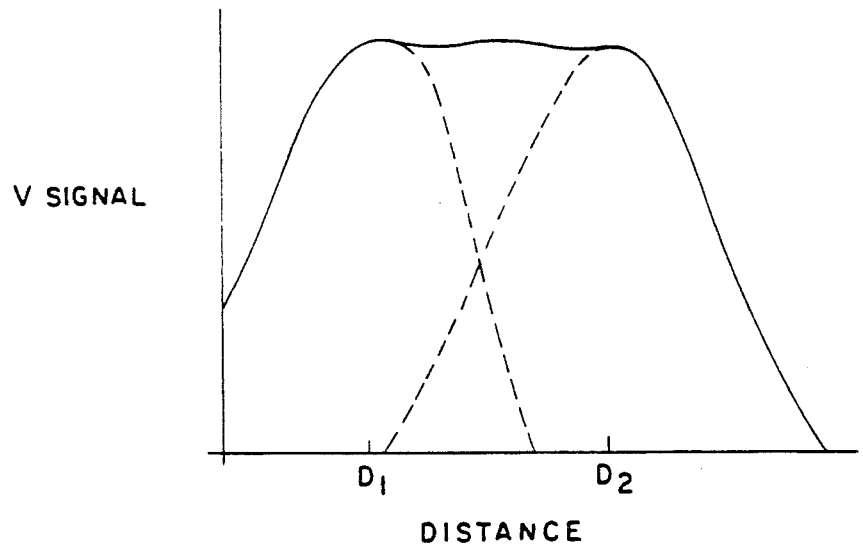
FIG. 6 is a graph illustrating the relative signal level of the photo detector output as a function of the target distance from the photo detector.
Figure 7:
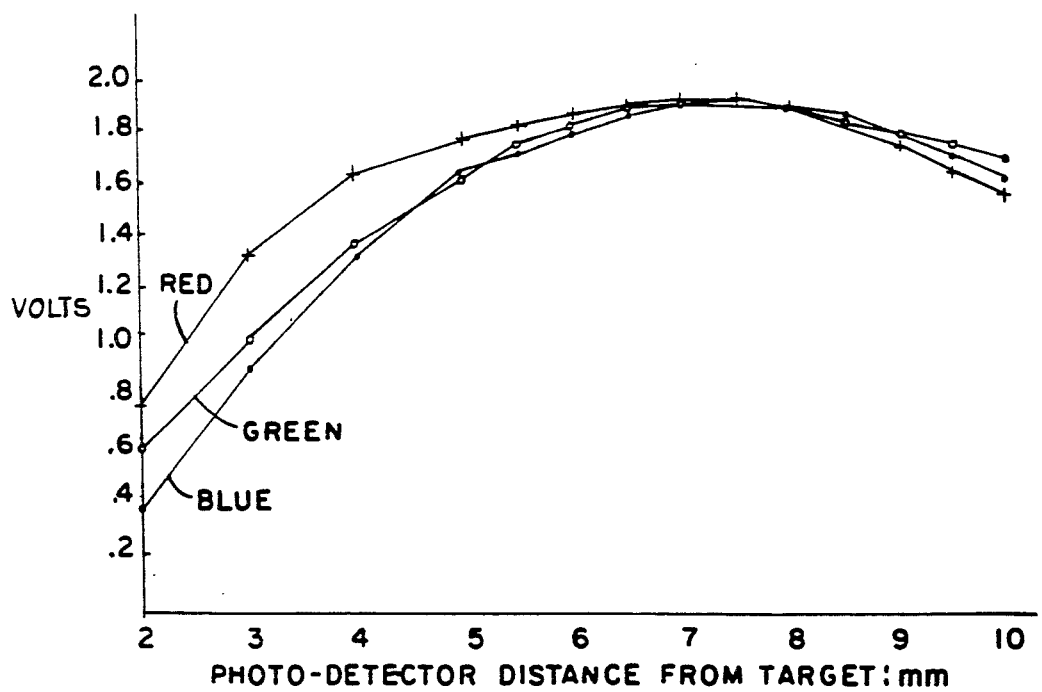
FIG. 7 is a plot of the signal output of the photo detector as a function of distance from the target for each of the discreet color beams of reflected light.
Figure 8:
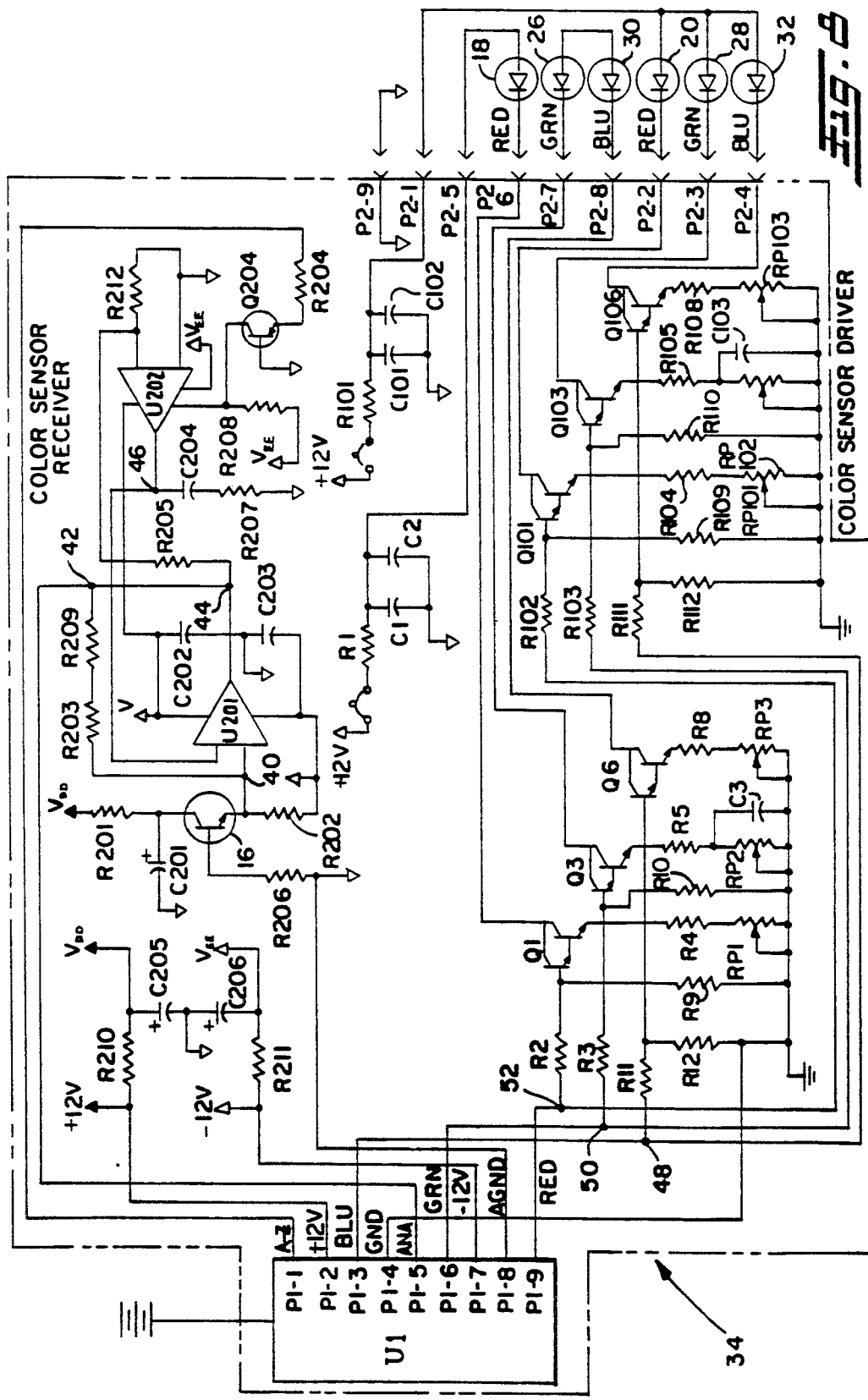
FIG. 8 is a schematic of the detector circuitry of the present invention.

Referring to FIG. 6, the signal from photo detector 16 is plotted conceptually as a function of the location of the target object to be sensed as locate directly beneath the photo detector 16 at the zone intermediate the distances $D_1$ and $D_2$. It will be seen from the graph of FIG. 6 that the relative strength of the signal of the photo detector 16 is not significantly affected by the location of the target article at any position between the distances $D_1$ and $D_2$.

A second pair of LEDs 26,28 emitting beams of a common chromaticity different from that of LEDs 18,20 is disposed diametrically opposed on opposites sides of detector 16 and circumferentially rotated from the LEDs 18,20. LEDs 26,28 are, respectively, received in apertures 22,24 provided in the base 12, with aperture 22 inclined at an angle $\theta_1$ and aperture 24 inclined at angle $\theta_2$ to the center line. In the present practice of the invention, the angle $\theta_1$ for aperture 22 is about 15° and the angle of inclination $\theta_2$ is about 45° which angles, by being substantially different, make the distance $D_2$ substantially greater than the distance $D_1$.

Referring to FIGS. 1, 2, and 3, a third pair of LEDs, 30,32 of common but different chromaticity is disposed diametrically opposed on opposite sides of the detector 16 and positioned circumferentially spaced intermediate the first and second pair of LEDs with the diode 32 inclined at an angle $\theta_1$ to the center line of the detector and the LED 30 inclined at an angle $\theta_3$ to the center line of the detector. In the presently preferred practice, the angle $\theta_1$ for LED 30 is about 15°, and the angle $\theta_3$ for LED 32 is about 40°.

Figure 4:
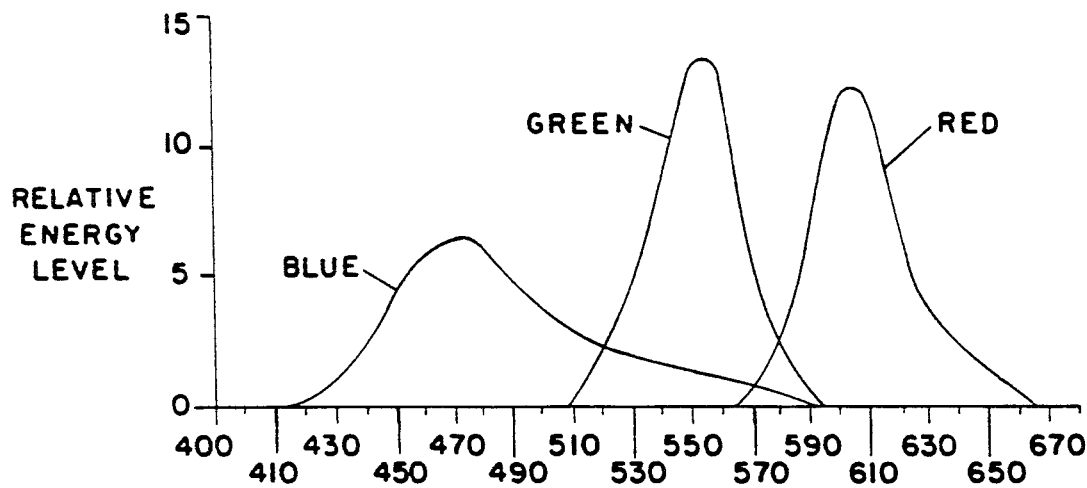
FIG. 4 is a plot of the 1 relative energy level of the light beams received by the photodetector as a function of the frequency of emitted light.

LEDs 18,20 have a common beam of generally red chromaticity, and LEDs 26,28 have a common beam of generally green chromaticity; whereas, LEDs 30,32 have a generally blue chromaticity. Referring to FIG. 4, values of the relative energy level of the output signal of the blue, green, and red LEDs employed in the present practice plotted as a function of wavelength in nanometers; and, the blue LED emits light of a center band or peak amplitude of 470 nanometers. The green LEDs emit light having a center band or peak level of energy at a wavelength of 555 nanometers; and, the red LEDs emit light having a center band or peak energy value wavelength of 610 nanometers.

Figure 9:
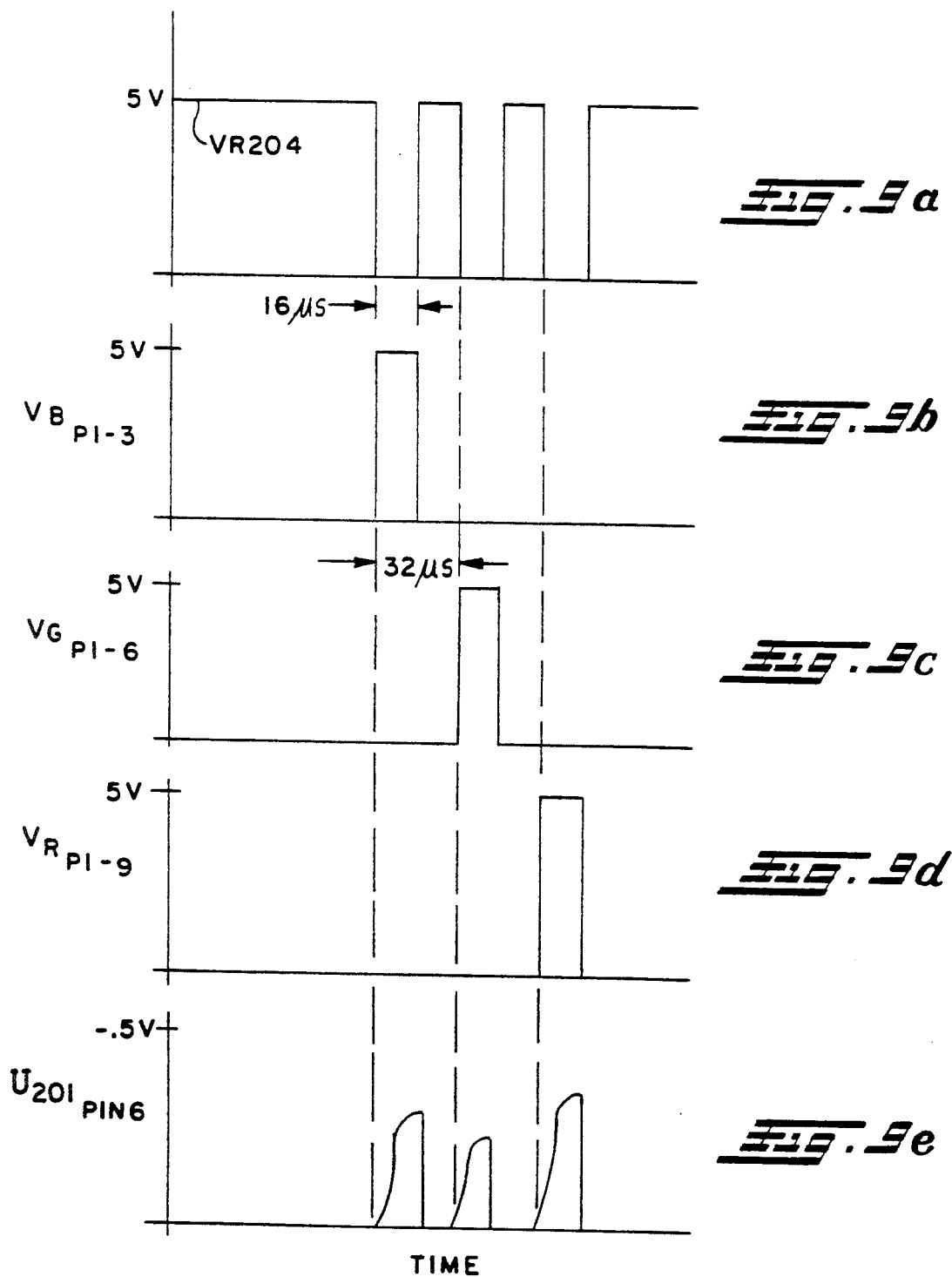
FIG. 9(a) is a timing diagram of the control pulse from the microprocessor.
FIG. 9(b) is a timing diagram showing the voltage applied by the microprocessor applied by the blue diodes.
FIG. 9(c) is a timing diagram showing the voltage pulse applied to the green LEDs.
FIG. 9(d) is a graph showing the voltage pulse applied to the red LEDs.
FIG. 9(e) is a timing diagram showing the voltage output of the operational amplifier associated with the photo detector.

Referring to FIGS. 7, 8, and 9(a) through 9(e), a microprocessor-based controller, indicated generally at 34, has a microprocessor U1 which provides a short-duration pulse on the order of 16 microseconds, as shown in FIG. 9(a) and 9(b), which is applied from pin P1-3 to junction 48 and the base of switch Q6 through resistor R11, and to the base of Q106 through resistor R111 to provide a timed pulse to the blue LEDs 30,32. The light emitted from the blue diodes 30,32 is reflected from a target object (not shown), passing beneath the photo detector 16, and is reflected onto the detector 16.

The photo detector 16 has its base grounded through R206 with the collector biased to the supply voltage $V_{DD}$ through R201; and, the emitter of detector 16 is connected through R202 to an input at pin 4 of a high-gain amplifier U201. Amplifier U201 is a commercially-available device obtainable from Motorola Semi Conductor Division, Schaumburg, Ill., and having manufacturer's designation MC-34080. The negative input at pin 2 of U201 is connected to junction 40, which is also connected to the emitter of detector 16 and to pin 5 of U1. Junction 40 is also connected through resistors R-203 and R-209 to junction 42 which is connected to P1-5 of U1 and also to junction 44.

The emitters of switches Q6 and Q106 are grounded respectively through resistors R8, RP3, and R108, RP103. The collector of Q6 is connected to the negative terminal of blue diode 30 and the collector of Q106 is connected to the negative side of the blue light emitting diode 32. The positive side of LEDs 30,32 are connected to a 12 volt source of supply through R-101, which is filtered by C101 and C102 connected to ground.

Upon receipt of the pulse of FIG. 9(b) to Q1 and Q106, the blue light from LEDs 30,32 as reflected from the target, causes the emitter of detector 16 to apply a signal to U201.

Amplifier U201 has its output pin 6 connected via junction 44 and 42 to pin P1-5 of U1. Junction 44 is also connected through R205 to the negative input at pin 2 of a transconductance amplifier U202 which, in the present practice comprises an RCA device bearing manufacturer's designation CA-3080, and which has the positive input grounded at pin 3. Resistor R212 is connected across the inputs of U202.

U202 is enabled by switch Q204, which receives a pulse signal from pin P1-1 of U1 through resistor R204, which is connected to the emitter of Q204, which has its base grounded; and, the collector of Q204 is connected to pin 5 of U202, which is biased at pin 4 thereof by supply voltage $V_{EE}$ and at pin 5 by $V_{EE}$ applied through R208. Capacitor C204 is connected through junction 46 to the output pin 6 of U202 and has the opposite side thereof grounded through R207. When amplifier R202 is turned "ON" by Q204, the output of U202 at pin 6 is forced to 0; and, the voltage on capacitor C204 is maintained at pin 3 the positive input of U201. U201 then responds only to the output of photo detector 16 a level representative of the amount of blue light reflected from the target from diodes 18,20; and the output of U-201 at pin 6 has a representative amplitude as shown by the first pulse in FIG. 9(e). When the signal from the controller at R-204 turns Q-204 "OFF" and U-202 is turned "OFF", capacitor C204 is charged to a −0.5 volts.

Subsequently, the green LEDs 26 and 28 are pulsed by a signal from pin P1-6 of U1, which is applied through junction 50 to resistor R3 to the base of switch Q3, which has its collector connected through the negative terminal of LED 26 and also connected through resistor R103 to the base of Q103, which has its collector connected to the negative terminal of green LED 28. Simultaneously, a pulse from U1 pin P1-1 to R204 repeats the operation of U202 and U201 as described above; and, the output of photo detector 16 results in the second pulse shown in FIG. 9(e).

Similarly, a subsequent pulse from U1 at output pin P1-9 is applied to junction 52 and through R2 to the base of Q1, whose collector is connected to the negative terminal of red LED 18; and, junction 52 is also connected through R-102 through the base of Q101, which has its collector connected to the negative terminal of red LED 20.

Illumination of the LEDs 18,20 causes light reflected from the target to activate the photo detector 16 to provide an output through U201 to junctions 42 and 44 and input pin P1-5 of U1 whose amplitude is indicative of the amount of reflected light as represented by the third pulse in time in FIG. 9(e). It will be understood that the operation of U202 and U201 in response to a pulse on R204 is identical to that described above with respect to the operation of the detector for each pair of red, blue, and green diodes.

The controller U1 includes a suitable analog-to-digital converter, which sums the three pulses for each of the red, green, and blue diode pairs, as shown in FIG. 9(e), in accordance with any suitable algorithm. In the present practice, it has been found satisfactory to sum the pulses for the red, green, and blue diodes numerically. However, a ratio algorithm may also be employed as follows:

$$x = V_R/(V_R + V_G + V_B);$$

$$y = V_G/(V_R + V_G + V_B).$$

where x and y are coordinates similar to the standard CIE-1931 chromaticity diagram, as well known in the art.

The designation and values for the various circuit components is given in table 1 below:

TABLE I

| REFERENCE NUMBER | TYPE | VALVE/ DESIGNATION |
|---|---|---|
| U1 | Microcomputer | |
| U201 | Op Amp | MC34080 |
| U202 | Op Amp | CA3080 |
| Q1, 2, 3 | Transistor | PETA 14 |
| Q101, 103, 106 | Transistor | PETA 14 |
| 18, 20 | Red LED | Stanley EAA55045 |
| 30, 32 | Blue LED | CREE C470-5C14 |
| 26, 28 | Green LED | STANLEY EBG5504S |
| 16 | Photo Transistor | OP805 |
| R1, 101 | Resistors | 10 |
| R2, 102 | Resistors | 2.74K |
| R3, 103 | Resistors | 2.37K |
| R4, 104 | Resistors | 15 |
| R5, 105 | Resistors | 10 |
| R8, 108 | Resistor | 6 |
| R9, 109 | Resistor | 1.69K |
| R10, 110 | Resistor | 1.87K |
| R11, 111 | Resistor | 1.77 |

TABLE I-continued

| REFERENCE NUMBER | TYPE | VALVE/ DESIGNATION |
|---|---|---|
| R12, 112 | Resistor | 1.38K |
| RP1, 101 | Potentiometer | 200 |
| RP2, 102 | Potentiometer | 50 |
| RP3, 103 | Potentiometer | 10 |
| R201 | Resistor | 1K |
| R202, 206 | Resistor | 100K |
| R203, 205 | Resistor | 10K |
| R204, 208 | Resistor | 7.5K |
| C1, 101, 204 | Capacitors | .1 uF, 50 v |
| C2, 102, 205, 206 | Capacitors | 10 uF, 16 v |
| C3, 103 | Capacitors | .047 uF |
| C201 | Capacitor | 6.8 uF, 16 v |
| C202, 203 | Capacitors | .047 uF, 50 v |

Figure 10:
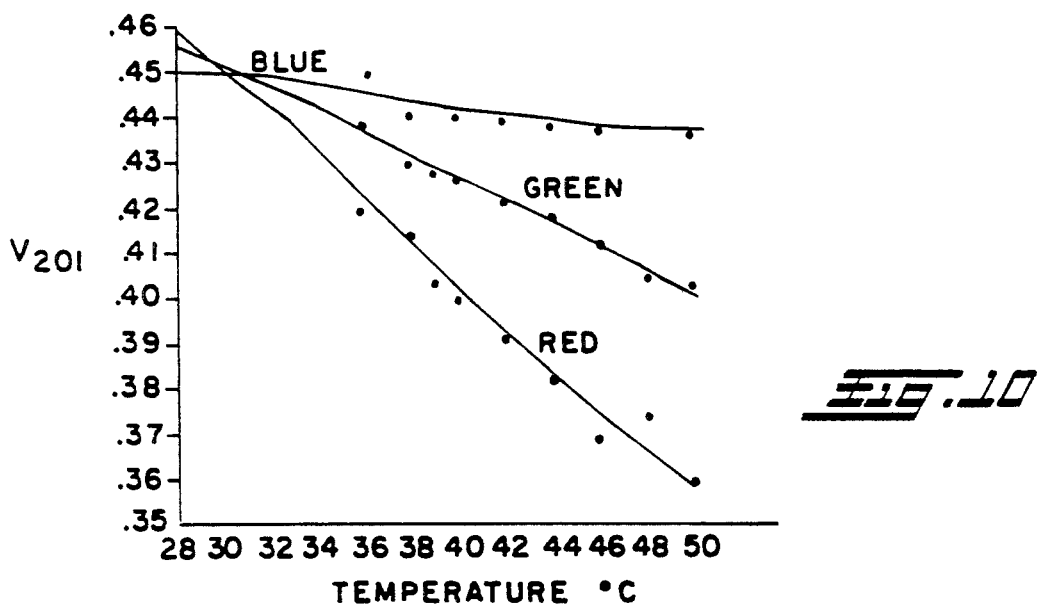
FIG. 10 is a graph plotted of values of detector output voltage as a function of ambient temperature, with separate plots for red, green, and blue LEDs.

Referring to FIG. 10, the characteristics of the red, blue, and green diodes as affected by variations in the ambient temperature are shown graphically. The voltage output of the photodetector at pin 6 of U201 is plotted as the ordinate; and, the ambient temperature in degrees Centigrade is plotted as the abscissa. The points plotted are connected to show the substantially linear relationship for each of the three colors of LEDs between the detected intensity of the reflected target light and the changes in ambient temperature of the LEDs. It will be apparent from the graphs of FIG. 10 that the red and green LEDs are the most affected by ambient temperature; whereas, the intensity of the light emitted from the blue LEDs is substantially constant over the range of temperatures typically experienced in service of photodetectors for manufacturing usage. The values of the voltage indicated as dots in the graph of FIG. 10 were obtained by placing the assembly of FIG. 1 and the circuit of FIG. 8 in an oven and varying the temperature and recording the voltage at the output pin 6 of U201.

Figure 11A:
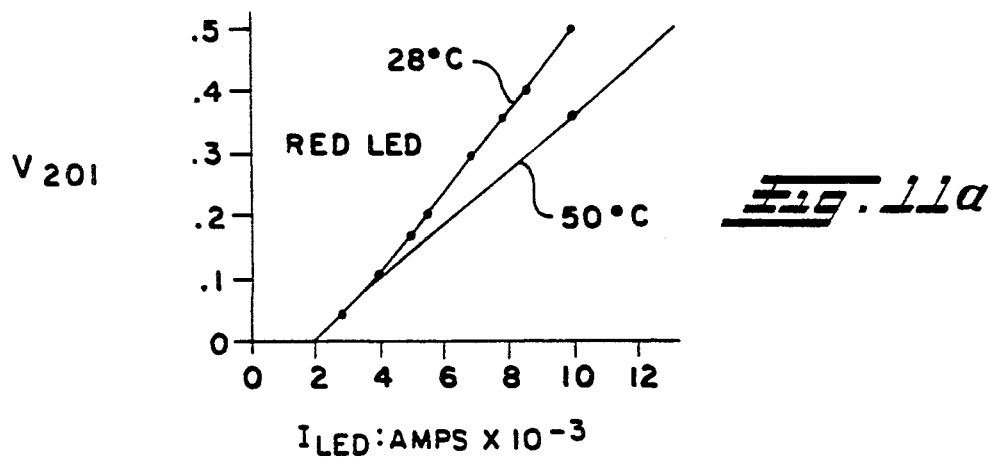
FIG. 11(a) is a graph plotted of detector output voltage versus LED current for red LEDs and different ambient temperatures; and, FIG. 11(b) is a graph similar to FIG. 11(a), plotted for green LEDs.

Referring to FIG. 11(a), the voltage at U201 pin 6 is plotted as the ordinate as a function of the current in milliamps supplied to a typical red LED such as LEDs 18, 20; and, two separate plots are illustrated: the upper curve is for a constant ambient temperature of 28° C., and the lower curve is plotted for values of voltage versus LED current at a constant ambient temperature of 50° C. Similar measurements were taken for typical green LEDs, such as LEDs 26, 28, and the values have been plotted in FIG. 11(b).

Referring to FIG. 10, the voltage drop over the temperature range 28° through 50° C. for the green LED is about 0.095 volts; and, the slope of the line connecting the measured values for the green LED is about −0.004 volts per degree Centigrade.

Figure 11B:
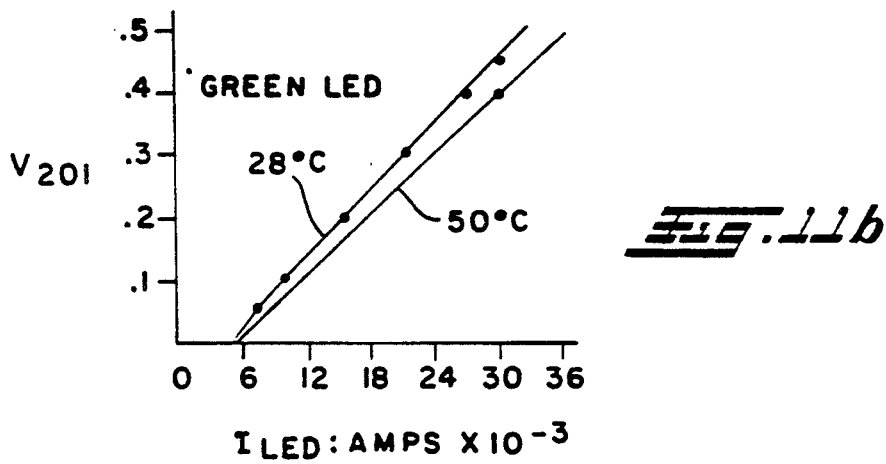

Referring to FIG. 11(b), it will be seen that at 50° C. an increase of current from 30 milliamps to 35 milliamps is required to raise the voltage output of U201 to 0.455 volts to restore the output to the level obtainable at 28° C. Thus, the correction ratio is $$\frac{35 \text{ ma}}{30 \text{ ma}} = 1.166 = C_R, \text{ the correction ratio.}$$

The voltage required to compensate may then be expressed by $$V_{50} = V_{28} + \frac{.004 \text{ v}}{°C.} \times (50° - 28°); \text{ or}$$

$$V_{50} = V_{28} + .088 \text{ volts.}$$

-continued $$\text{Therefore, } C_R = 1.166 = \frac{V_{28} + 0.088}{V_{28}} \text{; and, transposing,}$$

$$0.166 = \frac{.088}{V_{28}}. \text{ The voltage } V_{28} \text{ may thus be found:}$$

$$V_{28} = \frac{.0884}{.166} = 0.530 \text{ volts.}$$

The voltage $V_{28}$ is the voltage at the emitter of Q3 and Q103. For a typical Darlington device shown in FIG. 8, the base-to-emitter voltage is typically 1.3 volts across the internal junctions of the device. Thus the base voltage required to compensate for temperature is the sum of the emitter and base-to-emitter voltages, or 1.83 volts. Therefore, a 1.83 volt pulse is required at the base of Q1 and Q103 to directly compensate for temperature increases from 28° C. to 50° C.

The base voltage to Q3 and Q103 is controlled by the ratio of resistors R3 to R10 and R103 to R110 in accordance with the correction ratio $C_R$. Thus, by appropriate choice of the resistors R2, R9, and R103, R110, the green LEDs 26, 28 may be temperature compensated. It will be understood that similar correction is employed for the choice of resistors R2, R9, and R102, R109 for temperature compensating the red LEDs 18, 20 by correcting the voltage to the base of transistor switching devices Q1 and Q101.

It will further be understood that where blue LEDs have the temperature characteristics shown in the graph of FIG. 10, temperature correction of the blue LEDs is not necessary. However, if blue LEDs having different temperature characteristics are employed, and the change in voltage with changes in temperature is significant, the same correction procedure may be applied to the blue LEDs as is employed for the green LEDs, as previously discussed.

The present invention thus provides a unique and novel photoelectric color monitor which employs plural pairs of oppositely disposed LEDs of common chromaticity illuminating a target article disposed between a first and second target distance with LEDs of each pair are directed, such that the photodetector measures the optical sum of the reflected light from the target for each LED of the pair. The resultant signal generated by the photodetector is relatively insensitive to variations in distance of the target article to be sensed between the first and second target distance. The photodetector thus enables a single station detector or sensor to monitor the color of articles passing by where the distance of the article may vary from the detector between two predetermined limits. Each pair of LEDs emits light of different chromaticity within the visible spectrum to enable the detector to emulate the detection characteristics of the human eye. The color detector of the present invention is compensated for variations in ambient temperature experienced by the sensor.

Although the invention has hereinabove been described with respect to the illustrated embodiment, it will be understood that the invention is capable of modification and variation, and is therefore intended as limited only by the following claims.

We claim:
1. A photoelectric color sensor comprising:
   (a) at least one pair of angularly oppositely disposed electrically energizable light sources emitting beams of a common chromaticity, with one beam of said pair directed to intersect a first target area at a first predetermined angle, and the other beam of said pair directed to intersect a second target area disposed a selected distance substantially farther from said first target area at a second predetermined angle different from said first predetermined angle;
   (b) photodetector means disposed intermediate said ones of said pair and positioned to detect diffused reflections from an object located between said first and second target area and operative to provide an electrical signal indicative of the sum of said reflections;
   (c) means operative to intermittently energize said sources at common times, and said photodetector means receives the combined reflections of said pair of sources.

2. The color sensor defined in claim 1, further comprising a second and third pair of angularly oppositely disposed electrically energizable light sources with each pair emitting beams of a different discrete chromaticity.

3. The color sensor defined in claim 1, wherein said at least one pair includes a first pair of green light emitting sources, a second pair of red light emitting sources, and a third pair of blue light emitting sources.

4. The color sensor defined in claim 1, wherein said means operative to intermittently energize includes temperature compensating means operable to vary the energy level of said intermittent energization in accordance with a predetermined schedule in response to variations in ambient temperature.

5. The color sensor defined in claim 1, wherein said means operative to intermittently energize includes means for applying a voltage varied in accordance with a predetermined schedule in response to variations in ambient temperature.

6. A method of color detection comprising the steps of:
   (a) providing a pair of light-emitting sources of common chromaticity and disposing them in opposed arrangement;
   (b) directing the light from each one of said pair at a substantially different angular direction to a target area;
   (c) simultaneously energizing said pair and detecting the sum of the light from said pair reflected by an object placed within said target area;
   (d) generating an electrical signal indicative of said sum of reflected light; and,
   (e) comparing said signal with a reference level and indicating the difference therebetween.

7. A method of temperature compensating a color sensor comprising the steps of:
   (a) providing at least one light-emitting diode (LED) emitting a beam of light and a photo detector for receiving the output of said LED and emitting an electrical signal representative thereof;
   (b) energizing said LED and said detector and subjecting same to variations in ambient temperatures and determining the variation in said LED current required to maintain said detector signal constant as a function of temperature; and,
   (c) disposing an object to be sensed in said beam and detecting the reflection of said beam therefrom and altering the current in said LED in amount of said determined variation for the ambient temperature at the time of the detection of the beam from the object to be sensed.

* * * * *